(12) United States Patent
Katayama et al.

(10) Patent No.: US 8,020,445 B2
(45) Date of Patent: Sep. 20, 2011

(54) THREE-DIMENSIONAL ULTRASONIC IMAGING DEVICE

(75) Inventors: Masahiro Katayama, Tokyo (JP);
Hirokazu Karasawa, Kanagawa-Ken (JP); Motohisa Abe, Ibaraki-Ken (JP);
Takahiro Ikeda, Kanagawa-Ken (JP);
Yoshino Ito, Kanagawa-Ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 846 days.

(21) Appl. No.: 11/570,647

(22) PCT Filed: Jun. 13, 2005

(86) PCT No.: PCT/JP2005/010786
§ 371 (c)(1),
(2), (4) Date: Mar. 27, 2008

(87) PCT Pub. No.: WO2005/121771
PCT Pub. Date: Dec. 22, 2005

(65) Prior Publication Data
US 2008/0245150 A1  Oct. 9, 2008

(30) Foreign Application Priority Data
Jun. 14, 2004   (JP) .................... P2004-175873

(51) Int. Cl.
*G01N 29/06* (2006.01)
(52) U.S. Cl. ............................................... 73/602
(58) Field of Classification Search ............ 73/602
See application file for complete search history.

(56) References Cited

U.S. PATENT DOCUMENTS
5,143,075 A * 9/1992 Ishizuka .................... 600/447
(Continued)

FOREIGN PATENT DOCUMENTS
JP              59197854 A  * 11/1984
(Continued)

OTHER PUBLICATIONS
M. Abe et al., "Matrixeye™ Portable 3D Ultrasonic Inspection System," Toshiba Review, vol. 60, No. 4, Apr. 1, 2005, pp. 48-51.

*Primary Examiner* — Hezron E Williams
*Assistant Examiner* — Rose M Miller
(74) *Attorney, Agent, or Firm* — Foley & Lardner LLP

(57) ABSTRACT

The object of the present invention is to provide a the three-dimensional ultrasonic imaging apparatus for improving accuracy of internal inspection of an object to be inspected and enabling an automatic determination by means of ultrasonic waves. The three-dimensional ultrasonic imaging apparatus according to the present invention includes: an ultrasonic transducer having a plurality of piezoelectric vibrators; a driving element selecting portion for selecting a piezoelectric vibrator to emit an ultrasonic wave among a plurality of the piezoelectric vibrators; a signal detecting circuit for causing ultrasonic waves emitted by the selected piezoelectric vibrator to enter the object to be inspected, receiving echo reflected from the object to be inspected, and thereby detecting an electric signal corresponding to the reflected echo; a signal processing portion for generating three-dimensional imaging data by subjecting the electric signal corresponding to the detected reflected echo to parallel arithmetic processing; and a display processing device for receiving the three-dimensional imaging data from the signal processing portion, correcting image luminance of the three-dimensional imaging data so as to flatten imaging intensity distribution in the plane direction of the surface of the object to be inspected, and then displaying a corrected result.

6 Claims, 10 Drawing Sheets

U.S. PATENT DOCUMENTS

| | | |
|---|---|---|
| 6,618,510 B1 * | 9/2003 | Umiji .................. 382/260 |
| 2004/0024320 A1 | 2/2004 | Karasawa et al. |

FOREIGN PATENT DOCUMENTS

| JP | 2-42355 A | 2/1990 |
|---|---|---|
| JP | 4-336051 A | 11/1992 |
| JP | 09145694 A * | 6/1997 |
| JP | 11-118775 A | 4/1999 |
| JP | 2001-108661 A | 4/2001 |
| JP | 2002-48867 A | 2/2002 |
| JP | 2003-149213 A | 5/2003 |
| JP | 2004-53360 A | 2/2004 |
| JP | 2004337458 A * | 12/2004 |
| WO | WO 03/042686 A1 | 5/2003 |

* cited by examiner

THREE-DIMENSIONAL ULTRASONIC IMAGING DEVICE

TECHNICAL FIELD

The present invention relates to a three-dimensional ultrasonic inspection technology that performs three-dimensional non-destructive inspection of an internal structure, a state of a joined area and a state of a defect of an object to be inspected, using ultrasonic waves, and particularly, relates to a three-dimensional ultrasonic imaging apparatus that three-dimensionally visualizes the states of a defect, peeling, an oxidized film, a foreign material such as a void, and peeling of the joined area of the object to be inspected.

BACKGROUND ART

As an example of technologies concerning such a type of three-dimensional ultrasonic imaging apparatus, there is provided a stereoscopic ultrasonic inspection technology disclosed in Japanese Unexamined Patent Application Publication Nos. 2003-149213 and 2004-53360.

Since the three-dimensional ultrasonic imaging apparatus described in these patent documents includes an ultrasonic transducer in which a large number of piezoelectric vibrators are arranged in a matrix or an array, in a plane, using ultrasonic waves emitted and received by the ultrasonic transducer to and from the object to be inspected, it is possible to three-dimensionally visualize the states of a defect, peeling, an oxidized film, a foreign material such as a void, and peeling of a joined area of the object to be inspected, thus enabling inspection of the object to be inspected in a non-destructive manner.

Using a three-dimensional ultrasonic imaging apparatus utilizing the ultrasonic transducer including a large number of piezoelectric vibrators, it is possible to visualize the layer structure of the object to be inspected having a plurality of acoustic properties, and the states of defects, voids, and peeling, etc., by means of ultrasonic waves. However, since the imaging results of the three-dimensional image data obtained by processing an electric signal corresponding to the received reflected echo of the ultrasonic transducer become uneven according to the emitted and received patterns of the ultrasonic waves, it is difficult to determine the acceptability of the quality of the object to be inspected, correctly and quantitatively, it is therefore required to determine the inspection result by means of viewing, thus, resulting in fluctuations due to differences in opinion between individual examiners.

In a known three-dimensional image processing apparatus, for an ultrasonic image of the three-dimensional imaging data of the object to be inspected obtained by processing an electric signal corresponding to the received reflected echo of the ultrasonic wave emitted and received by the ultrasonic transducer:

(1) since the imaging data of a three-dimensional ultrasonic image becomes uneven according to the emitted and received patterns of the ultrasonic wave, it has been difficult to perform objective and quantitative inspection;

(2) since the defects in an object to be inspected are determined by means of viewing, time and manpower are required, thus resulting in possibility of occurrence of fluctuations in the determination conditions of inspection; and (3) by using a single or a pair of ultrasonic transducers arranged in a matrix, by calculating in advance the propagation time according to propagation and refraction of an ultrasonic signal emitted and received by the transducers and generating a table, it has been required to achieve a high speed and high accuracy angle beam method when an angle beam method for performing defect testing of an object to be inspected with a curved surface or defect inspection of a welded portion is performed.

DISCLOSURE OF THE INVENTION

The present invention was conceived in consideration of the circumstances encountered in the prior art mentioned above and an object of the present invention is to provide a three-dimensional ultrasonic imaging apparatus that enables to improve the accuracy and processing speed of internal inspection of an object to be inspected by means of ultrasonic waves, and automatically determine acceptability of the quality of the object to be inspected, at a time, for example, when inspection of internal defects of the object to be inspected having a curved shape such as a circular cylinder, or an angle beam method etc. of the welding portion having beads on the surface thereof is performed.

The three-dimensional ultrasonic imaging apparatus, in order to achieve the above-mentioned objects, includes: an ultrasonic transducer in which a plurality of piezoelectric vibrators are disposed in a matrix or an array; a driving element selecting portion connected to the piezoelectric vibrators for selecting a piezoelectric vibrator to emit an ultrasonic wave from the ultrasonic transducer among a plurality of the piezoelectric vibrators; a signal detecting circuit for causing an ultrasonic wave emitted by the piezoelectric vibrator selected by the starting element selecting portion via an acoustic wave propagating medium to enter the object to be inspected, receiving the reflected echo from the object to be inspected, and thereby detecting an electric signal corresponding to the reflected echo; a signal processing portion for generating three-dimensional imaging data by subjecting the electric signal corresponding to the detected reflected echo to parallel arithmetic processing while causing the inside of the object to be inspected to correspond to mesh elements in an three-dimensional imaging region partitioned in advance; a display processing device for displaying a corrected result by receiving three-dimensional imaging data from the signal processing portion, correcting image luminance of the three-dimensional imaging data so as to flatten imaging intensity distribution in the plane direction of the surface of the object to be inspected, and then displaying a corrected result.

In the above-mentioned preferable example of three-dimensional ultrasonic imaging apparatuses according to the present invention, the display processing device includes: a luminance correction circuit for correcting luminance of three-dimensional imaging data taken from the signal processing portion by multiplying a correction function in an (X, Y) plane direction which is set so as to flatten the imaging intensity distribution of the surface of the object to be inspected of the three-dimensional imaging data taken from the signal processing portion, to the value of the three-dimensional imaging data; and a display portion for displaying the three-dimensional imaging data whose luminance is corrected by the luminance correction circuit.

Further, the display processing device may include an arithmetic determination circuit for generating a sliced image sliced in a plane direction of the three-dimensional imaging data corresponding to the mesh elements in the three-dimensional imaging region of the object to be inspected, as a sliced image, calculating the number of imaging mesh elements having intensity equal to or greater than a set value of each sliced image, and performing abnormal determination of the object to be inspected from the positions and the areas of anomalous portions such as defects, so as to display the determined result on the display portion.

Furthermore, the three-dimensional ultrasonic imaging apparatus of the present invention, which is provided in order to achieve the above-mentioned objects, includes: an ultrasonic transducer in which a plurality of piezoelectric vibrators are disposed in a matrix; a driving element selecting portion which is connected to the piezoelectric vibrators from the ultrasonic transducer, and selects a piezoelectric vibrator to emit ultrasonic waves by selectively driving a plurality of the piezoelectric vibrators; a signal detecting circuit for causing an ultrasonic wave emitted by the piezoelectric vibrator selected by the starting element selecting portion via an acoustic wave propagating medium to enter the object to be inspected and receiving the reflected echo from the object to be inspected to detect an electric signal of the reflected echo; a signal processing portion for receiving the electric signal of the detected echo, subjecting the electric signal to image synthesizing processing to generate three-dimensional imaging data; and a display device for receiving the three-dimensional imaging data from the signal processing portion to display the result of the image synthesizing processing; the signal processing portion performs image synthesizing of the state of the object to be inspected on the basis of a detection time with which the signal detecting circuit detects the driving signal of the piezoelectric vibrators as a reflected echo, and the matrix-like special arrangement of the piezoelectric vibrators.

In the preferable example of three-dimensional ultrasonic imaging apparatuses according to the above present invention, at the signal processing portion, it is preferable for all of the piezoelectric vibrators constituting the ultrasonic transducer to perform image synthesizing of the surface shape and internal state of the object to be inspected by selecting imaging data from the electric signals of the reflected echo from the object to be inspected on the basis of two-way ultrasonic wave propagation time data obtained by selecting a pair of pieces of table data corresponding to the combination of emission and reception from a plurality pieces of table data in which ultrasonic propagation time of one propagating direction is stored and adding a pair of pieces of the table data to each of three-dimensional imaging mesh elements corresponding to the three-dimensional imaging data in the object to be inspected from the piezoelectric vibrators via the acoustic propagating medium.

Further, it is desirable for the signal processing portion to be configured with a boundary setting portion for setting and memorizing the surface shape of the object to be inspected, a table data generating portion for storing the ultrasonic wave propagating time from the piezoelectric vibrator to the three-dimensional imaging mesh elements on the surface of the object to be inspected and inside the object to be inspected via the acoustic propagating medium, and generating table data in which the one-way ultrasonic wave propagating times are stored for all of the piezoelectric vibrators, an image synthesizing portion for receiving wave form data recorded the wave form storing memory and the table data via an A/D converter and synthesizing an three-dimensional image.

Furthermore, the signal processing portion may be configured so as to visualize the internal state of the object to be inspected by inputting a boundary extracting portion for receiving the result of imaging the surface of the object to be inspected and automatically extracting the surface shape, the surface shape generated by the boundary extracting portion, and coordination information of the piezoelectric vibrators in the table data generating portion.

Furthermore, the signal processing portion selects and adds two table data corresponding to a pair of piezoelectric vibrators for emission and reception selected when collecting waveform data, one by one, with respect to all waveform data collected among a plurality of table data generated in the table data generation portion, and on basis of the two-way ultrasonic wave propagation time obtained from the addition result, by subjecting the three-dimensional imaging mesh elements to allocation processing of the corresponding waveform data and addition processing, one by one, three-dimensional images may also be synthesized.

Moreover, the table data generating portion of the signal processing portion, by storing the differencing processing result of the depth direction using that the one-way ultrasonic wave propagation time changes continuously in the depth direction, the data capacity of the one-way ultrasonic wave propagation time table can also be compressed.

In addition, by generating table data while intimately fixing a wedge type shoe material to the ultrasonic transducer via a couplant so as to fix the ultrasonic transducer to the object to be inspected with an angle, it is also possible to three-dimensionally visualize the internal state of the object to be inspected by emitting and receiving ultrasonic waves with the angle.

Furthermore, by generating table data while preparing a pair of the ultrasonic transducers and fixing them to the surfaces of the object to be inspected so as to face each other symmetrically with an angle, and using one of a pair of the ultrasonic transducers for emission and the other one for reception, it is also possible to three-dimensionally visualize the internal state of the object to be inspected.

Furthermore, internal cross-sectional images of the object to be inspected can also be three-dimensionally imaged, by using an ultrasonic transducer in which piezoelectric vibrators are arranged in a line, to display by visualizing the internal cross-sectional images of the object to be inspected one by one and by superposing a plurality of the obtained cross-sectional images along the axis of a rotational angle, while two-dimensionally visualizing the surface shape of the object to be inspected, receiving the obtained cross-sectional imaging data in a boundary extracting portion of the signal processing portion, automatically extracting the surface shape in the boundary extracting portion every time when the object to be inspected is rotated by a constant angle, and regenerating the (two-dimensional) table data.

According to the present invention of the characters mentioned above, it is possible to provide a more even and easily visible display image by correcting three-dimensional imaging data synthesized by an three-dimensional ultrasonic imaging apparatus including an ultrasonic transducer. Moreover, it is possible to display anomalous portions such as internal defects or voids of the object to be inspected, objectively and quantitatively, and to automatically and quantitatively determine the acceptability of the quality of the object to be inspected, quickly and correctly.

Further, the nature and further characteristic features of the present invention will be made clearer from the following descriptions of preferred embodiment made with reference to the accompanying drawings.

BEST MODE FOR EMBODYING THE INVENTION

Embodiments of a three-dimensional ultrasonic imaging apparatus according to the present invention will be described hereunder with reference to the accompanying drawings.

Figure 1:
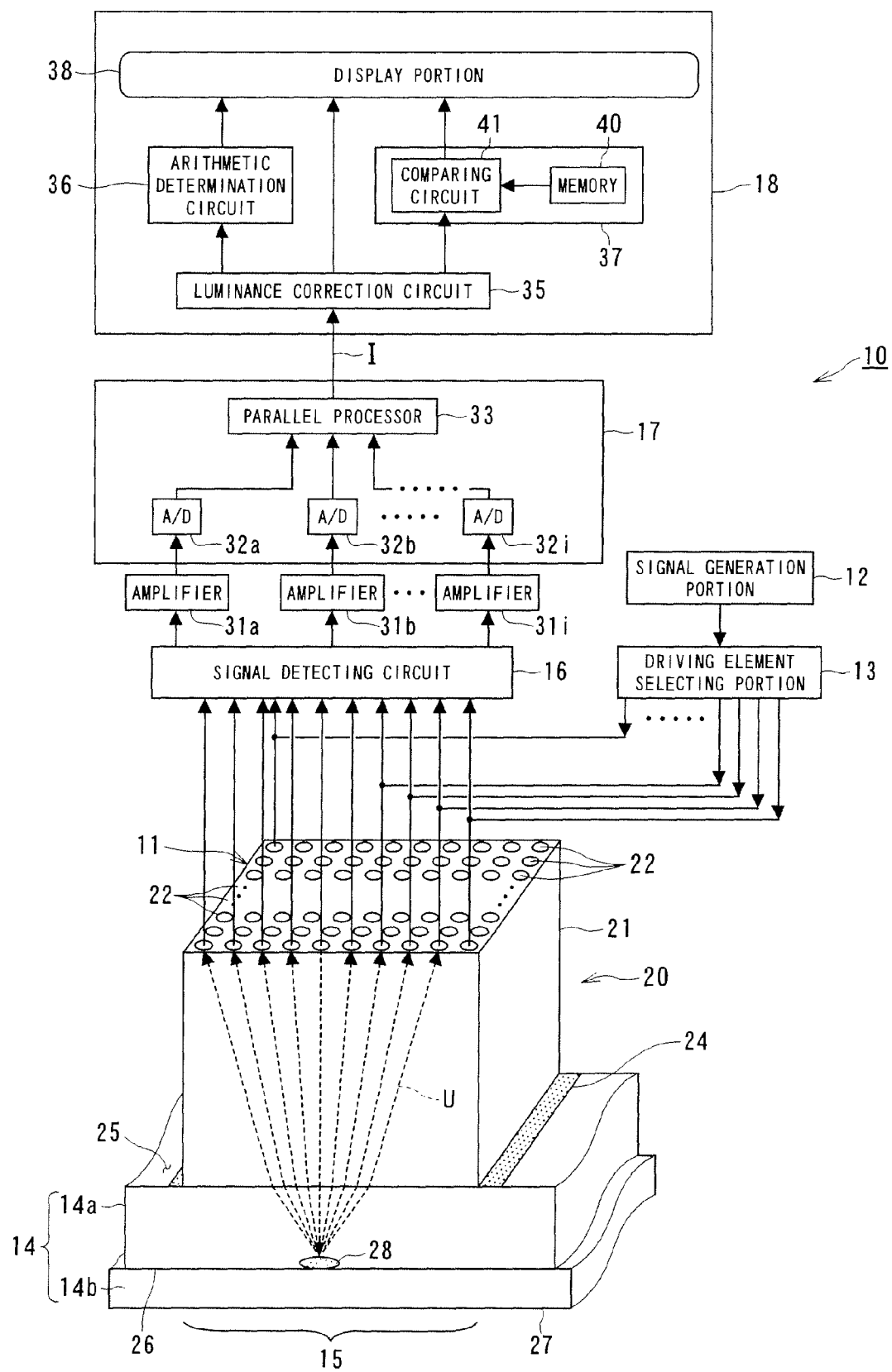
FIG. 1 is a view showing an entire configuration of a three-dimensional ultrasonic imaging apparatus according to a first embodiment of the present invention.

FIG. 1 is a view showing a configuration of a first embodiment of a three-dimensional ultrasonic imaging apparatus according to the present invention.

The three-dimensional ultrasonic imaging apparatus 10 functions as an ultrasonic camera which can perform precise stereo imaging of an internal structure and defect shape of an object to be inspected. The three-dimensional ultrasonic imaging apparatus 10 includes: an ultrasonic transducer 11 for converting an ultrasonic vibration into an electric signal and vice versa and for emitting and receiving an ultrasonic wave with a prescribed frequency; a signal generating portion 12 for generating a driving signal which drives the ultrasonic transducer 11; a driving element selecting portion 13 for selecting the driving signals from the signal generating portion 12 and selectively driving piezoelectric vibrators of the ultrasonic transducer 11; a signal detecting circuit 16 for irradiating ultrasonic wave emitted by the ultrasonic transducer 11 to a inspection region 15 of an object to be inspected 14 and for detecting an electric signal corresponding to the reflected echo from the inspection region 15 via the ultrasonic transducer 11; a signal processing portion 17 for generating three-dimensional (3D) ultrasonic imaging data by subjecting the electric signal corresponding to the reflected echo detected by the signal detecting circuit 16 to parallel arithmetic processing; and a display processing device 18 for subjecting the three-dimensional ultrasonic imaging data and the display image processed in the signal processing portion 17 to correction processing and comparing processing, determining the state of the internal defect 28 of the object to be inspected 14 automatically with high accuracy, and displaying the determined result.

Moreover, the three-dimensional ultrasonic imaging apparatus 10 includes a sensing device for an ultrasonic inspection apparatus 20 which can display the internal structure of the object to be inspected 14 by rapidly capturing high sensitivity and highly accurate three-dimensional ultrasonic images, and the ultrasonic imaging apparatus 10 enables high speed inspection that requires an image to be captured every one to ten seconds. The ultrasonic inspection apparatus 20 includes an ultrasonic transducer 11 as an ultrasonic sensor for emitting and receiving ultrasonic waves, and an acoustic propagating medium 21 is brought into close contact with the emitting and receiving surface as a sensing surface of the ultrasonic transducer 11.

The three-dimensional ultrasonic imaging apparatus 10 can be applied for testing of the maintenance state of a welded portion and the presence or absence (non-presence) of weld defects in car, aviation and railroad industries, and for observing the state of a welded portion in plant and shipbuilding industries.

The ultrasonic transducer 11 is configured as an ultrasonic sensor composed of a matrix sensor where a large number of piezoelectric vibrators 22 are independently aligned and arranged in a matrix having m rows and n columns. It is possible to collect several thousands of or several dozens of thousands of ultrasonic waveforms of the reflected echoes simultaneously by means of an ultrasonic camera (the three-dimensional ultrasonic imaging apparatus 10) including the ultrasonic sensor 11, and it is also possible to perform imaging of the internal structure of the object to be inspected 14, the state of a joined area 15, and the presence or non-presence of and the state of weld defects, at a high speed.

A drive signal generated from the signal generating portion 12 is selected by the driving element selecting portion 13 and applied to the each piezoelectric vibrator 22 of the ultrasonic transducer 11. The driving orders of the piezoelectric vibrators 22 are determined one by one or several ones by several ones at a time by means of selection of the driving element selecting portion 13, and the piezoelectric vibrators 22 are driven at a desired drive timing. In place of being arranged in a matrix, the array of the piezoelectric vibrators 22 may be arranged in rows or in crossed lines so as to constitute an array sensor. In other words, the ultrasonic sensor constituting the ultrasonic transducer 11 may be a matrix sensor or an array sensor.

A liquid or solid acoustic wave propagating medium 21 is brought into close contact with the surface for emitting and receiving ultrasonic waves, which is a sensing surface of the ultrasonic transducer 11, specifically, on the side of the object to be inspected 14. A couplant 24 for acoustic matching of the ultrasonic waves, is provided between the acoustic wave propagating medium 21 and the object to be inspected 14, as occasion demands. The couplant 24 is formed of a gelled liquid or solid having a low volatility. When the acoustic wave propagating medium 21 is a liquid, the couplant 24 is not required.

Moreover, the acoustic wave propagating medium 21 acting as a shoe material is box-shaped overall having an opening area formed in accordance with the size of the inspecting region (target region) 15 of the object 14, the height of the acoustic wave propagating medium 21 is determined by the oscillation angle (spreading angle) of the ultrasonic wave emitted by the piezoelectric vibrators 22.

As for the object to be inspected 14, for example, two plate-like structures 14a and 14b, joined by means of spot welding, are used, and the inspecting region 15 of the structures 14a and 14b is subjected to internal inspection in a non-destructive manner by the three-dimensional ultrasonic imaging apparatus 10 using ultrasonic waves. As for the object to be inspected 14, a multiple layer structure having three or more plate-like structures welded by being superposed may be used. Moreover, the object to be inspected 14 may be a metallic material, a resin material, or a specimen to be tested.

Meanwhile, the signal generating portion 12 is a unit or like for supplying a drive signal to the ultrasonic transducer 11 in order to generate ultrasonic waves by actuating the piezoelectric substances of the piezoelectric vibrators 22, and generates a pulsed or continuous drive signal. In other words, when a piezoelectric vibrators 22mn arranged in m-th row and n-th column to be driven by the driving element selecting portion 13 is selected, the generated drive signal is supplied to the selected piezoelectric vibrators 22mn at a required timing. Since the driving element selecting portion 13 sequentially selects one or a plurality of the piezoelectric vibrators 22mn to be driven at the required timing, when the drive signal from the signal generating portion 12 is supplied to the selected piezoelectric vibrators 22mn, the piezoelectric vibrators 22mn are driven so as to emit an ultrasonic wave U toward the object to be inspected 14 due to the piezoelectric characteristics thereof.

The ultrasonic waves sequentially emitted by the piezoelectric vibrators 22 of the ultrasonic transducer 11, pass through the acoustic wave propagating medium 21 acting as a shoe member, enter the inspection region 15 of the object 14 via the couplant 24, and are reflected at boundary layers of the inspection region 15.

The echoes reflected by the boundary layers such as the upper surface 25, boundary surfaces (the bottom surface of the object to be inspected 14a and the upper surface of the object to be inspected 14b) 26, the bottom surface 27, the weld defect portion 28 of the object 14, from the object 14 via the acoustic wave propagating medium 21, are received by the piezoelectric vibrators 22 of the ultrasonic transducer 11, acting as an ultrasonic sensor, with different time lags, vibrate the piezoelectric vibrators 22, and are converted into electric signals corresponding to the reflected echoes. Subsequently, the electric signals corresponding to the reflected echoes are input to the signal detecting circuit 16, in which the electric signals corresponding to the reflected echoes are each detected with respect to the corresponding piezoelectric vibrator 22.

In the three-dimensional ultrasonic imaging apparatus 10, when a drive signal is supplied to the piezoelectric vibrators 22mn selected by the driving element selecting portion 13, among the piezoelectric vibrators 22 of the ultrasonic transducer 11, the selected piezoelectric vibrators 22mn operate so as to emit ultrasonic waves U. The emitted ultrasonic waves U are irradiated to the inspecting region 15 of the object to be inspected 14 via the acoustic wave propagating medium 22 and the couplant 24, provided if necessary. Portions of the ultrasonic waves U irradiated to the inspecting region 15 of the object to be inspected 14 are reflected from a density boundary layer of the inspecting region 15 and are reflected as echoes. The reflected echoes are returned to the matrix sensor (ultrasonic transducer) 11, via the couplant 24 and the acoustic wave propagating medium 21, and received by the corresponding piezoelectric vibrators 22 with different time lags. The reflected echoes are converted into electric signals by means of piezoelectric transformation performed by the piezoelectric vibrators 22, sent to the signal detecting circuit 16 and detected.

In the ultrasonic transducer 11, since the piezoelectric vibrators 22 are sequentially driven at a required timing by the drive signals which are sequentially supplied from the drive signal selecting portion 13, the reflected echoes of the ultrasonic waves emitted by the piezoelectric vibrators 22 are received by the matrix sensor 11 acting as an ultrasonic sensor in a two dimensional-manner.

In the matrix sensor 11, if m rows and n columns of the piezoelectric vibrators 22 consist of, for example, 10×10 elements, one hundred piezoelectric vibrators 22 are disposed in a matrix, and the piezoelectric vibrators 22mn are sequentially driven by the driving element selecting portion 13. If the drive signals are sequentially supplied to the piezoelectric vibrators 22, the ultrasonic waves U are sequentially emitted by the piezoelectric vibrators 22 at the driving timing. The reflected echoes of the ultrasonic waves sequentially emitted by the piezoelectric vibrators 22 are sequentially received by the matrix sensor 11 acting as an ultrasonic sensor, and electric signals corresponding to the reflected echoes, which are the received signals thereof, are sent to the signal detecting circuit 16 every time the reflected echoes are received.

Consequently, the reflected echoes of the ultrasonic waves, emitted by the individual piezoelectric vibrators 22 disposed in a matrix by means of operation of the ultrasonic transducer 11 are received by the matrix sensor 11 in a two-dimensional manner. The matrix sensor 11 receives the reflected echoes corresponding to the ultrasonic waves emitted by the individual piezoelectric vibrators 20mn, the electric signals corresponding to the received reflected echoes are sent to the signal detecting circuit 16, and sent to the signal processing portion 17 via the signal detecting circuit 16.

The signal detecting circuit 16 has a function of detecting the electric signals corresponding to the reflected echoes emitted by the matrix sensor 11. Among the detected signals, a plurality of signals required for inspection are each supplied to the signal processing portion 17 via amplifiers 31a, 31b, . . . , and 31i. The amplifiers 31a, 31b, . . . , and 31i may be provided to the signal processing portion 17.

The amplifiers 31a, 31b, . . . , and 31i amplify the supplied electric signals corresponding to the reflected echoes to decibel (dB) values which can be subjected to signal processing, for example, to an order of 10,000 times that of the supplied electric signals, and the amplified electric signals are supplied to corresponding A/D converters 32a, 32b, . . . , and 32i, which convert an analog signal to a digital signal. The A/D converters 32a, 32b, . . . , and 32i have functions of subjecting the supplied electric signals to A/D conversion, and of supplying the converted electric signals to corresponding parallel processors 33a, 33b, . . . , and 33i.

The parallel processors 33 in the signal processing portion 17 include a three-dimensional image generating portion, which is a unified processor, rapidly subjects the digital signals supplied from the A/D converters 32a, 32b, . . . , and 32i to arithmetic processing in parallel, each of them specifying reflection intensity from a corresponding one of mesh elements partitioned in the inspection region (imaging region) in advance, and generates three-dimensional imaging data I which visualizes the meshed internal state of the object to be inspected 14. The generated three-dimensional imaging data I is sent from the parallel processors 33 to the display processing device 18.

The parallel processors 33 in the signal processing portion 17 have a function of generating three-dimensional imaging data I for visualizing the state of the joined area 15 by processing the digital signals supplied from the A/D converters 32a, 32b, . . . , and 32i. The three-dimensional imaging data I is generated by causing the electric signals corresponding to the reflected echoes, detected by the signal detecting circuit 16, to each correspond to one of the mesh elements of the three-dimensional imaging region set inside the object to be inspected 14 by means of opening-synthesizing processing.

Moreover, the three-dimensional image generating portion 34 of the parallel processors 33, generates three plane (two-dimensional) images by viewing through the three-dimensional imaging data I from three directions, which are a front (X-Y plane) direction viewed from the ultrasonic transducer 11 and two directions (Y-Z plane) and (Z-X plane) perpendicular to the front direction and each other, and projecting the largest data value of the imaging data, superposed in the through-view directions of the three-dimensional imaging data I, in the three directions on a plane.

The display processing device 18 includes: a luminance correction circuit 35 for correcting the image luminance distribution of three-dimensional imaging data I supplied from the signal processing portion 17; an arithmetic determination circuit 36 for dividing the measured three-dimensional imaging data I into aggregates of sliced images Is in horizontal direction, calculating the positions and the areas or the volumes of anomalous portions from the ultrasonic wave reflection intensity distribution of each sliced image Is, and automatically determining the acceptability of the quality of the object to be inspected 14; a difference determining circuit 37 for automatically detecting anomalous portions such as defects by subjecting the reference imaging data of the object to be inspected 14 and the calculated three-dimensional imaging data I to differencing processing; and a display section 38 for displaying the three-dimensional imaging data I subjected to luminance correction and the automatically determined result of the object to be inspected 14. As for the arithmetic determination circuit 36 and the differencing determining circuit 37, only one of them may be included.

The luminance correction circuit 35 in the display processing portion 18 has a function of correcting the luminance distribution so as to eliminate the fluctuations of the luminance distribution occurring in the three-dimensional imaging data I sent from the signal processing portion 17 and to flatten the luminance distribution of images.

Figure 2A:
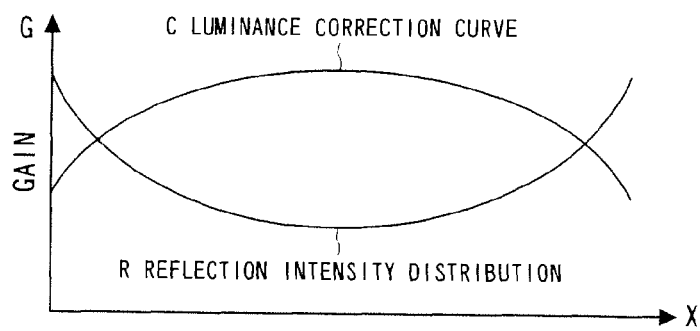
FIG. 2A is a view showing an example of image correction processing of a display processing device in the three-dimensional ultrasonic imaging apparatus shown in FIG. 1.
Figure 2B:
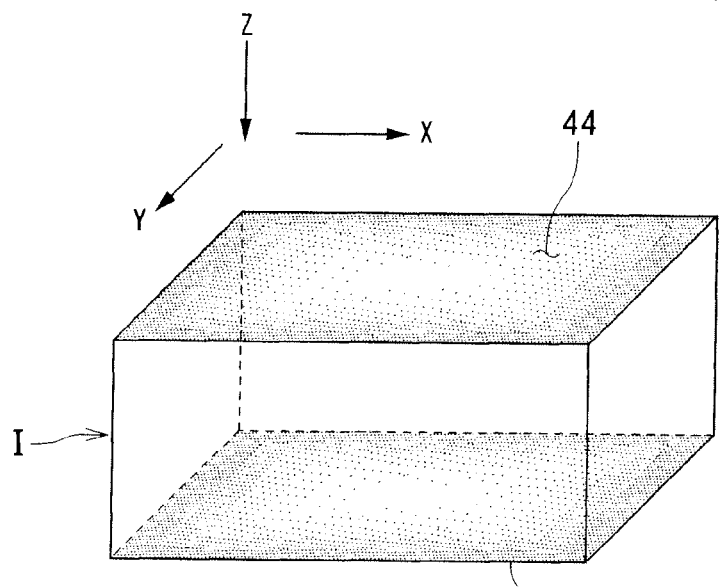
FIG. 2B is a view showing an example of image correction processing of a display processing device in the three-dimensional ultrasonic imaging apparatus shown in FIG. 1.

In the three-dimensional imaging data I generated by the parallel processor 33 of the signal processing portion 17, since irradiation of ultrasonic waves by the emitted and received patterns by piezoelectric vibrators 22 of the ultrasonic transducer 11 is uneven, the fluctuations occur in the luminance distribution of surface images of the object to be inspected 14. The surface images 44 of the object to be inspected 14 are represented in a similar manner as the reflection intensity distribution R of ultrasonic waves in a distribution chart in FIG. 2A in which gain is shown along the vertical axis and the X-direction is the horizontal direction, and the surface images 44 of the three-dimensional imaging data I, as shown in FIG. 2B, tend to be strong at the center and to be weak at the periphery.

Figure 2C:
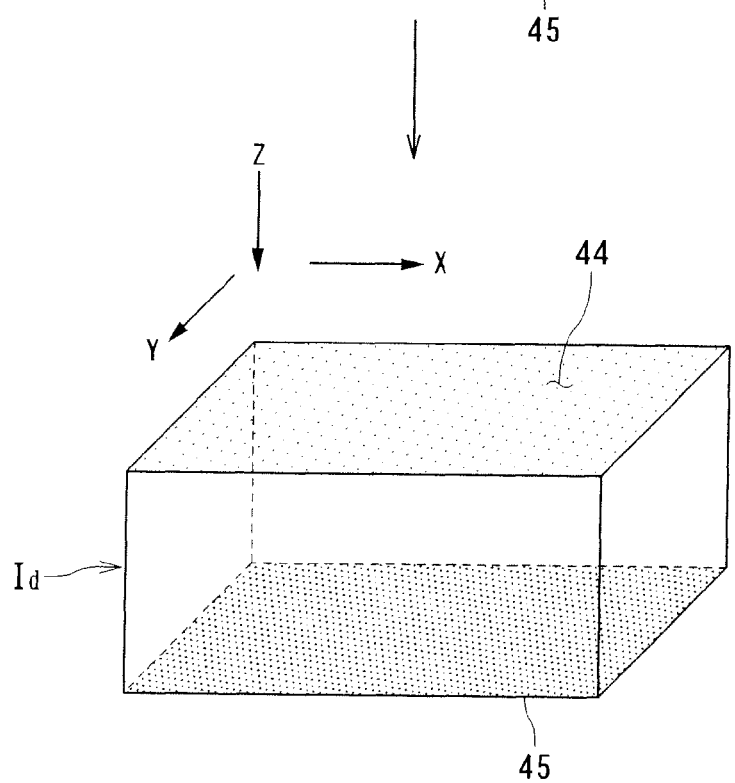
FIG. 2C is a view showing an example of image correction processing of a display processing device in the three-dimensional ultrasonic imaging apparatus shown in FIG. 1.
Figure 3A:
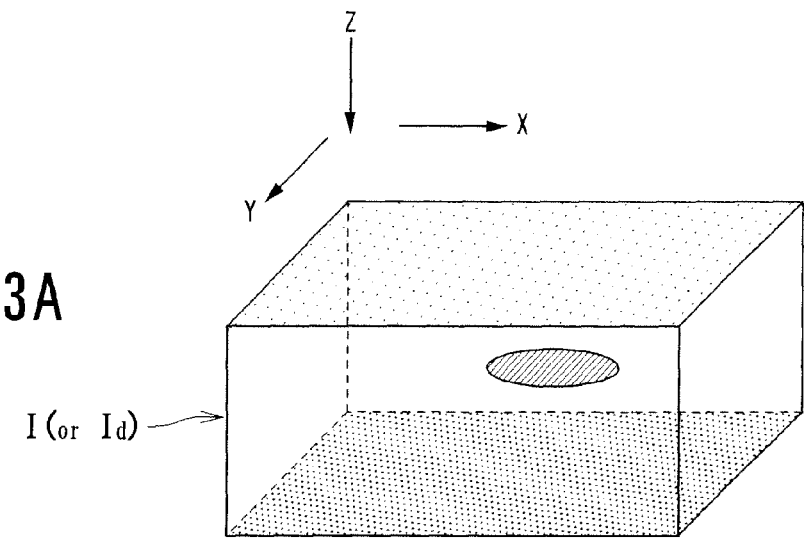
FIG. 3A is a view showing an example of automatic determination processing of an arithmetic determination circuit in a display processing device equipped with the three-dimensional ultrasonic imaging apparatus of the present invention.
Figure 3B:
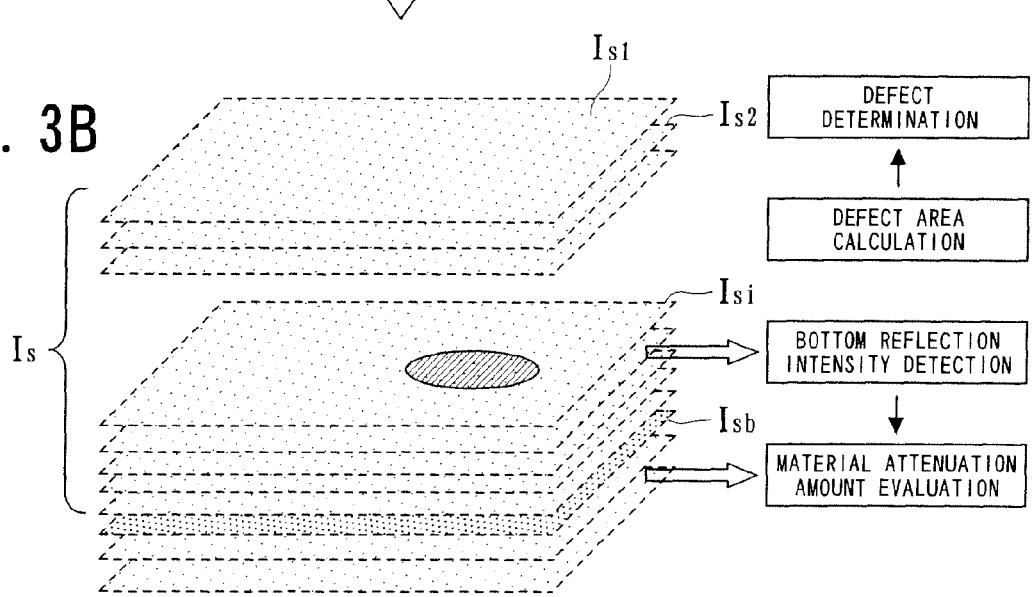
FIG. 3B is a view showing an example of automatic determination processing of an arithmetic determination circuit in a display processing device equipped with the three-dimensional ultrasonic imaging apparatus of the present invention.

Consequently, luminance correction of the image of the three-dimensional imaging data I is performed so as to obtain an image with even luminance distribution shown in FIG. 2C, by flattening the three-dimensional imaging data I using a luminance calibrating curve C, which is a correction function in a plane (X,Y) direction so as to be, for example, the inverse value of the reflection intensity distribution R, so that adverse effects due to the fluctuations in the luminance distribution do not appear so as not to generate differences in intensity due to reflection intensity distribution R of the ultrasonic waves in the surface images 44 of the object to be inspected 14. The result of luminance correction of the image of the three-dimensional imaging data I is represented as a stereo display image Id in the display portion 38.

The luminance correction circuit 35 of the display processing portion 18 has a function of obtaining a uniform image Id without the fluctuations of luminance values through emission and reception of ultrasonic waves by piezoelectric vibrators 22mm of the ultrasonic transducer 11 by correcting luminance values of the three-dimensional imaging data I so as to flatten the distribution, in a plane direction, of the three-dimensional imaging data I, obtained by subjecting an endless numbers of reflected echoes from the inside of the object 14 to opening synthesizing processing.

In other words, the luminance correction circuit 35 of the display processing portion 18, by amplifying the imaging data values (luminance values) of the three-dimensional (3D) imaging data I corresponding to mesh elements in the three-dimensional imaging region of the object to be inspected 14, in accordance with the distribution in the horizontal direction (X, Y direction) thereof, by performing correction of influence of the surface reflection wave of the object 14 and by performing attenuation correction of the ultrasonic waves in the object 14 can display a processed three-dimensional display image Id of the object 14 on the display portion 38, which has no fluctuation of luminance and which is more uniform and easier to be viewed.

Moreover, for the three-dimensional imaging data I or Id representing the reflection intensity of an ultrasonic wave, the arithmetic determination circuit 36 in the display processing device 18, in order to automatically determine the presence or non-presence of internal defects 28 of the object to be inspected 14, subjects the three-dimensional images of the three-dimensional imaging data Id to dividing processing so as to obtain sliced images Is which are cut in the horizontal (X, Y direction) direction. The three-dimensional images obtained after processing divide the three-dimensional images before processing of the three-dimensional imaging data I into aggregates of sliced images Is containing a top surface image Is1 to a bottom surface image Isb.

The number of the mesh elements of the sliced images Is is determined as a stereo mesh number determined in the object to be inspected 14 in advance, and accordingly, by calculating the number of imaging mesh elements whose imaging luminance is equal to or greater than a set value set in advance, the position and the area of the object 14 is obtained.

The non-processed three-dimensional image is divided into sliced images Is cut in the horizontal direction by the arithmetic determination circuit 36, after being processed, the three-dimensional positions (3D positions) and the areas or the volumes of anomalous portions such as defects, whose reflection intensity of the ultrasonic waves is equal to or greater than a set value, are obtained objectively and quantitatively from the intensity distribution of the reflected waves of sliced images Is by means of calculation of the number of the imaging mesh elements, and acceptability of the quality of the object to be inspected 14 can be automatically determined.

Moreover, since the bottom surface of the object to be inspected 14*a* (the interface 26 of the object) has a large ultrasonic wave reflection intensity due to the density difference thereof, the large ultrasonic wave reflection intensity appears on the bottom surface image Ib of an object to be inspected 14*a* as a magnitude (brightness) of the imaging luminance. Consequently, by quantitatively observing the imaging luminance of the bottom surface portion of the object to be inspected 14*a*, voids and minute defects occurred inside the object 14, can be evaluated quantitatively and accurately by counting the number of imaging mesh elements of the sliced images Is.

Further, the display processing device 18 includes a difference determining circuit 37 for automatically determining anomalous portions such as internal defects of the object to be inspected 14. In the difference determining circuit 37, three-dimensional imaging data of a normal object to be inspected (a work-piece) obtained in advance, is stored in a memory 40 as reference values (reference imaging data), in advance. By comparing the stored reference imaging data with the measured three-dimensional imaging data I (or Id) by means of a comparison circuit 41 and by subjecting the stored reference imaging data to differencing processing, anomalous portions 48 such as internal defects of the object to be inspected 14 are extracted, and, thus, acceptability of the quality of the object 14 is automatically determined.

Figure 4A:
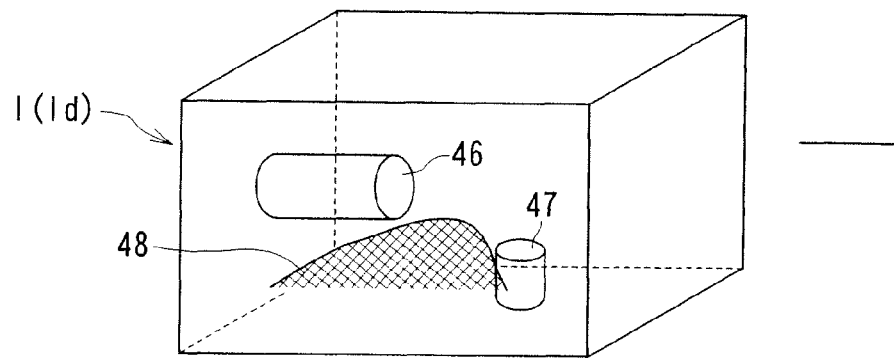
FIG. 4A is a view showing an example of automatic determination processing of a difference determining circuit in the display processing device equipped with the three-dimensional ultrasonic imaging apparatus of the present invention.
Figure 4B:
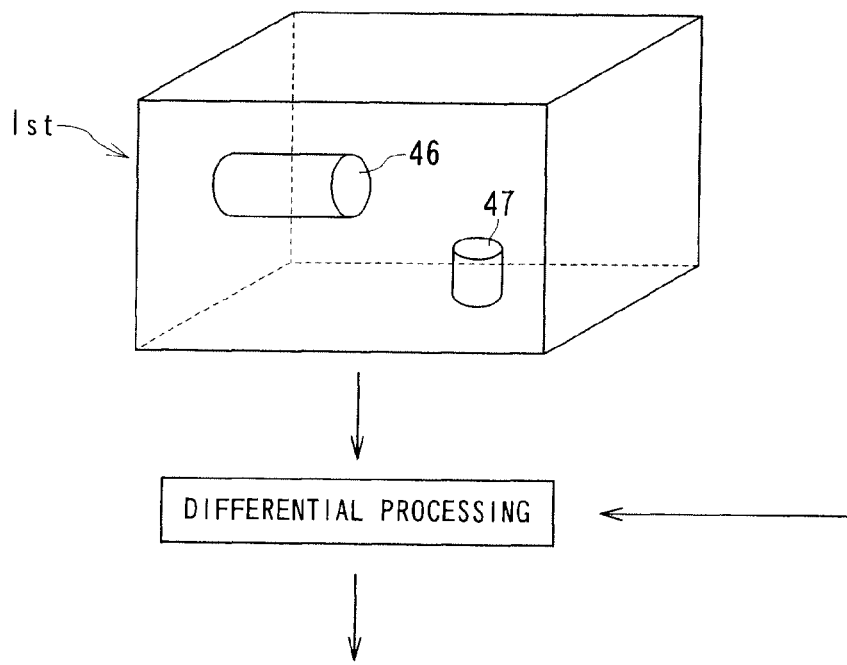
FIG. 4B is a view showing an example of automatic determination processing of a difference determining circuit in the display processing device equipped with the three-dimensional ultrasonic imaging apparatus of the present invention.

Specifically, the difference determining circuit 37 includes the comparison circuit 41 and the memory 40, while the measured three-dimensional imaging data I (Id) shown in FIG. 4A is sent to the comparison circuit 41, the reference imaging data shown in FIG. 4B, stored in the memory 40 is supplied to the comparison circuit 41, then, subjected to differencing processing. The three-dimensional imaging data I is composed of data values corresponding to the mesh elements inside the three-dimensional imaging region of the object to be inspected 14.

Figure 4C:
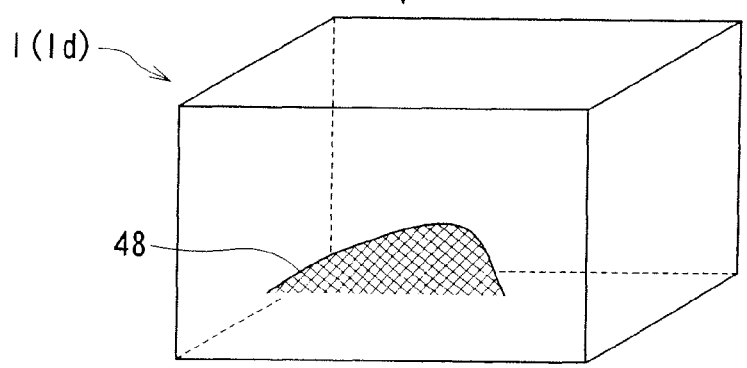
FIG. 4C is a view showing an example of automatic determination processing of a difference determining circuit in the display processing device equipped with the three-dimensional ultrasonic imaging apparatus of the present invention.

By subjecting the measured three-dimensional imaging data I in FIG. 4A, and the reference imaging data shown in FIG. 4B, as shown in FIG. 4C, to differencing processing, a fixed image due to anomalous portions 48 such as internal defects and the shape of the object to be inspected 14, is identified, and by determining the number and the positions of the imaging mesh elements whose difference is equal to or greater than a set value set in advance, it is possible to automatically detect the three-dimensional positions and areas or volumes of the anomalous portions 48 such as internal defects of the object to be inspected 14. These detected results are shown in the display portion 38. In addition, in FIGS. 4A and 4B, reference numerals 46 and 47 denote processed three-dimensional shape images.

In the embodiment of the present invention, since the three-dimensional imaging data I synthesized by a three-dimensional ultrasonic imaging apparatus including an ultrasonic transducer 11 composed of plurality of piezoelectric vibrators 22 formed in a matrix or an array, independently, is subjected to correction processing by the luminance correction circuit 35 of the display processing device 18, by combining a plurality of the imaging data obtained while moving the ultrasonic transducer 11 in accordance with the position of the ultrasonic transducer 11, it is possible to perform three-dimensional imaging processing enabling the image to be more even and more easily understood.

Further, by calculating the number and positions of the imaging mesh elements having luminance equal to or greater than a set value from sliced images formed from three-dimensional imaging data I sliced in the horizontal direction, by comparing the reference imaging data of the three-dimensional imaging of a normal work-piece of the object to be inspected 14 and the measured three-dimensional imaging data, and then, by subjecting them differencing processing, it is possible to automatically determine the three-dimensional positions and sizes (areas or volumes) of the defect portions such as internal defects of the object to be inspected 14, thus enabling automatic identification of acceptability of the object to be inspected 14.

Meanwhile, as mentioned before, the object of the present invention is to provide a mechanism for performing an inspection by using a three-dimensional ultrasonic imaging apparatus having a configuration and an action as mentioned above, shown in FIG. 1, and specifically, the three-dimensional ultrasonic imaging apparatus, when defects of an object to be inspected having a curved surface are inspected, will be described as a second embodiment of the present invention hereunder with reference to FIGS. 5 and 6, in which like reference numerals are denoted to the same components as those in the three-dimensional ultrasonic imaging apparatus shown in FIG. 1, and the detailed description thereof will be omitted.

Figure 5:
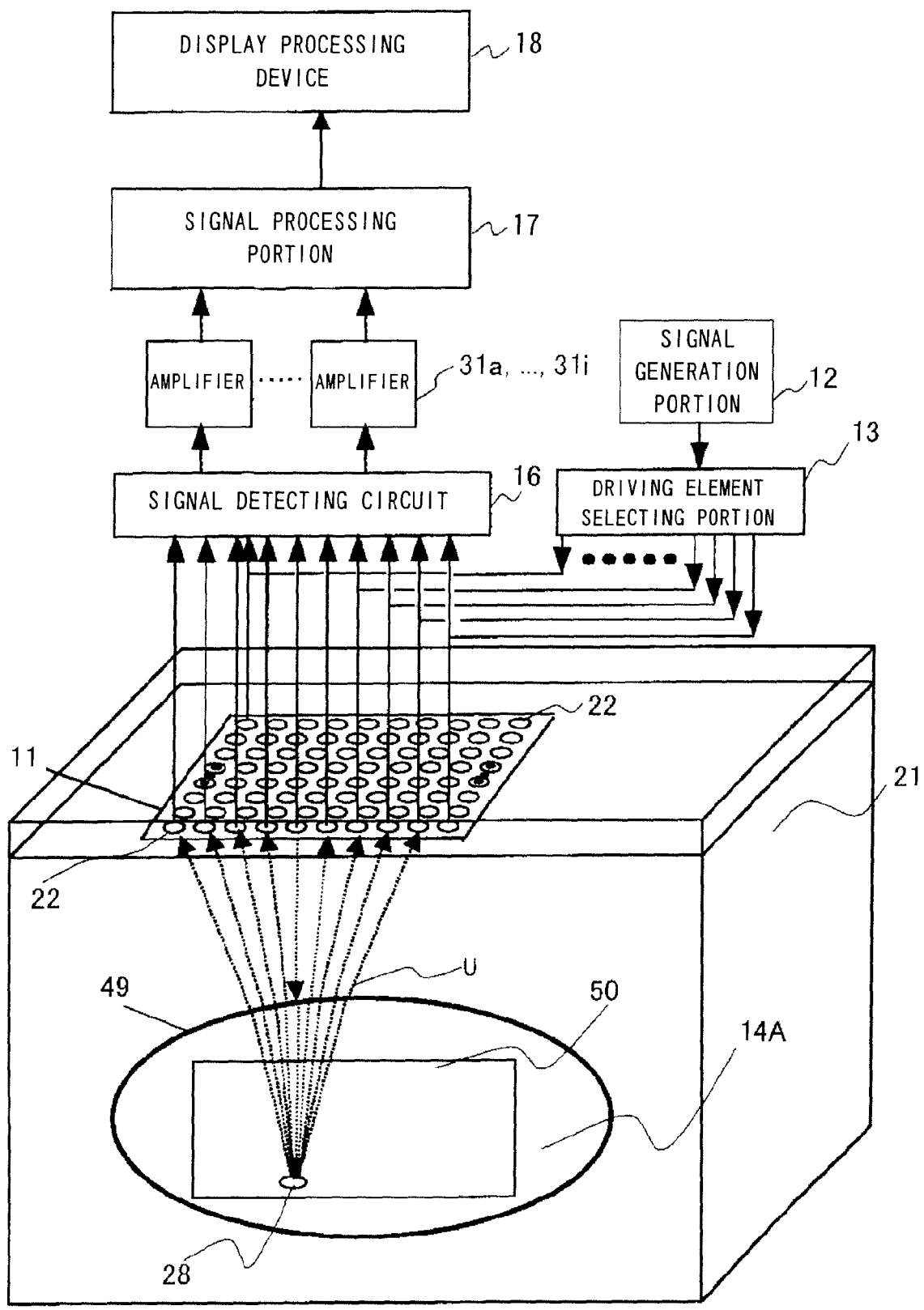
FIG. 5 is a view of an entire configuration showing a three-dimensional ultrasonic imaging apparatus according to a second embodiment of the present invention.
Figure 6:
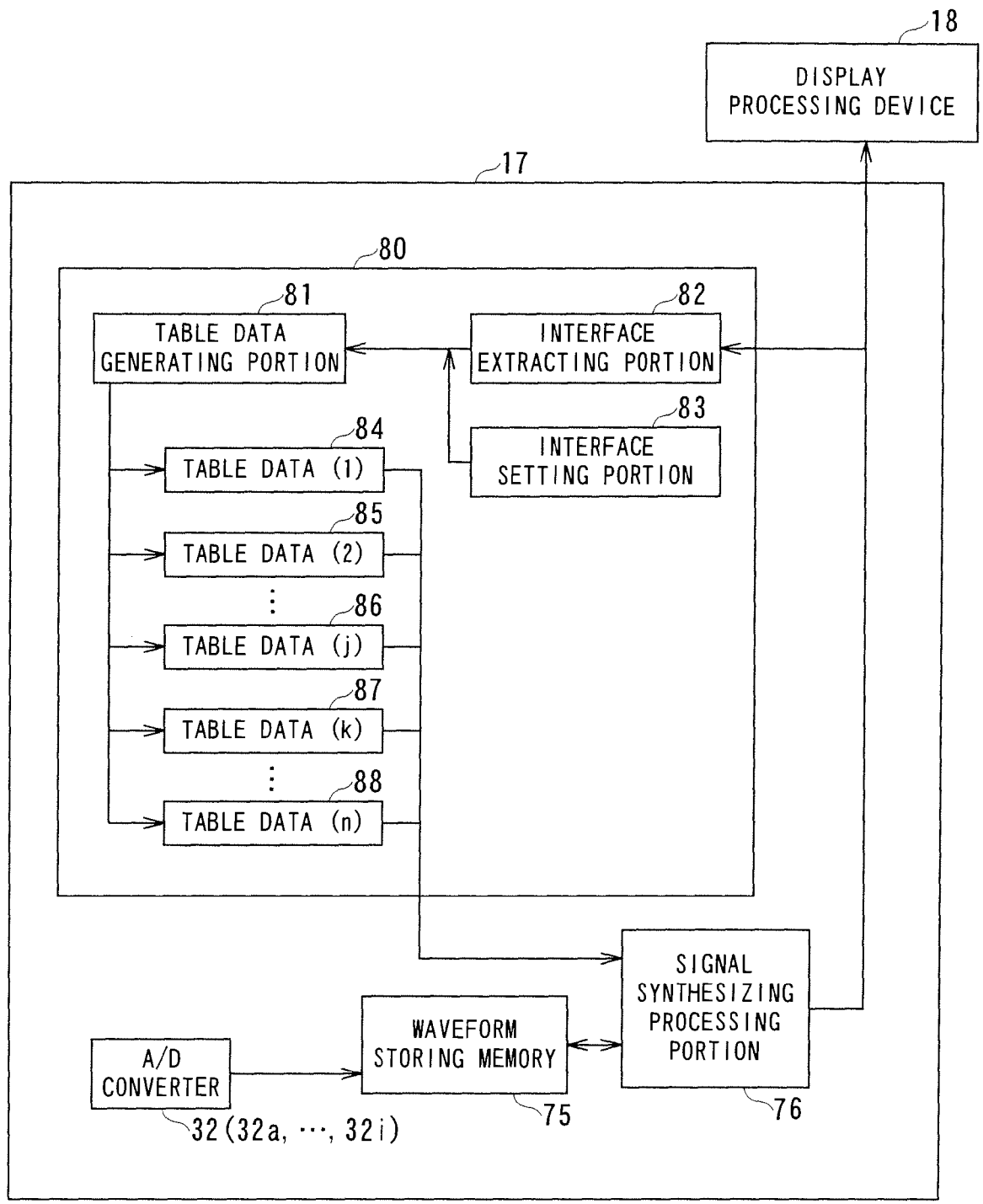
FIG. 6 is a view of a configuration of a signal processing portion in FIG. 5.

As shown in FIG. 5, the three-dimensional ultrasonic imaging apparatus includes an ultrasonic transducer (matrix sensor) 11, a signal generating portion 12, a driving element selecting portion 13, a signal detecting circuit 16, amplifiers 31*a*, - - -, and 31*i*, a signal processing portion 17 and a display processing device 18. The front surface of the ultrasonic transducer 11 is directly brought into contact with an acoustic wave propagating liquid medium 21, and receives ultrasonic waves U reflected by the defects 28 in the object to be inspected 14A. In the ultrasonic transducer 11, n pieces of piezoelectric vibrators 22, - - -, 22 are arranged in a matrix, among of which piezoelectric vibrators to be driven are determined by selection of the driving element selecting portion 13, and a drive signal from the signal generating portion 12 is supplied by a lead. Moreover, electric signals emitted by respective piezoelectric vibrators 22 are supplied to the signal detecting circuit 16 by a lead.

If the piezoelectric vibrator 22 are electrically driven, due to the properties as a piezoelectric substance, ultrasonic waves are emitted, and the emitted ultrasonic waves U propagate through the acoustic wave propagating medium 21 and reach to the defects 28 in the object to be inspected 14A after being refracted by a curved surface interface 49. Ultrasonic waves U reflected by the defects 28, after being refracted again by the curved surface interface 49, enter the piezoelectric vibrator 22 via the acoustic wave propagating medium 21, and consequently, each of the piezoelectric vibrators 22 emits an electric signal.

The signal generating portion 12 has a function of generating pulsed or continuous drive signals so that the piezoelectric vibrators 22 generate ultrasonic waves U. The generated drive signal is supplied to the driving element selecting portion 13.

The drive signal selection portion 13 selects one or a plurality of piezoelectric vibrators 22 to be driven and then supplies a driving signal supplied by the signal generating portion 12 to the selected piezoelectric vibrators 22. The signal detecting circuit 16 detects the electric signals generated by the piezoelectric vibrators 22. A plurality of electric signals among the detected signals, required for inspection, are sequentially supplied to the corresponding amplifiers 31 (31*a*, - - - , 31*i*). The A/D converter 32 subjects the supplied electric signals to A/D conversion, temporarily stores the signals in a waveform storing memory 75 in the signal processing portion 7, and then supplies them to an image synthesizing processing portion 76. The image synthesizing processing portion 76 generates information that processes the digital signal supplied by the waveform storing memory 75, and visualizes a state of the object to be inspected. The generated information is supplied to the display processing device 18 and displayed on the display portion 38.

Meanwhile, in a table data generating portion 81 of an unifying processor 80, on the basis of the data of the curved boundary 49 generated by an interface extracting portion 82 and the data of the coordinates of the piezoelectric vibrators 22, - - - , 22, n pieces of table data (1) 84 to table data (n) 88 are generated, in which one-way ultrasonic wave propagating time, that is required for the signals to be emitted by respective piezoelectric vibrators 22, refracted by the curved boundary 49 and reach to all imaging mesh elements in an imaging region 50, is stored.

In addition, in the interface extracting portion 82, the positional data of the curved surface boundary 49 can be automatically generated by subjecting the imaging result of the object of to be inspected 14A, taken in advance and generated in the image synthesizing processing portion 76 to extraction processing of the surface position of the object to be inspected 14A.

Figure 7:
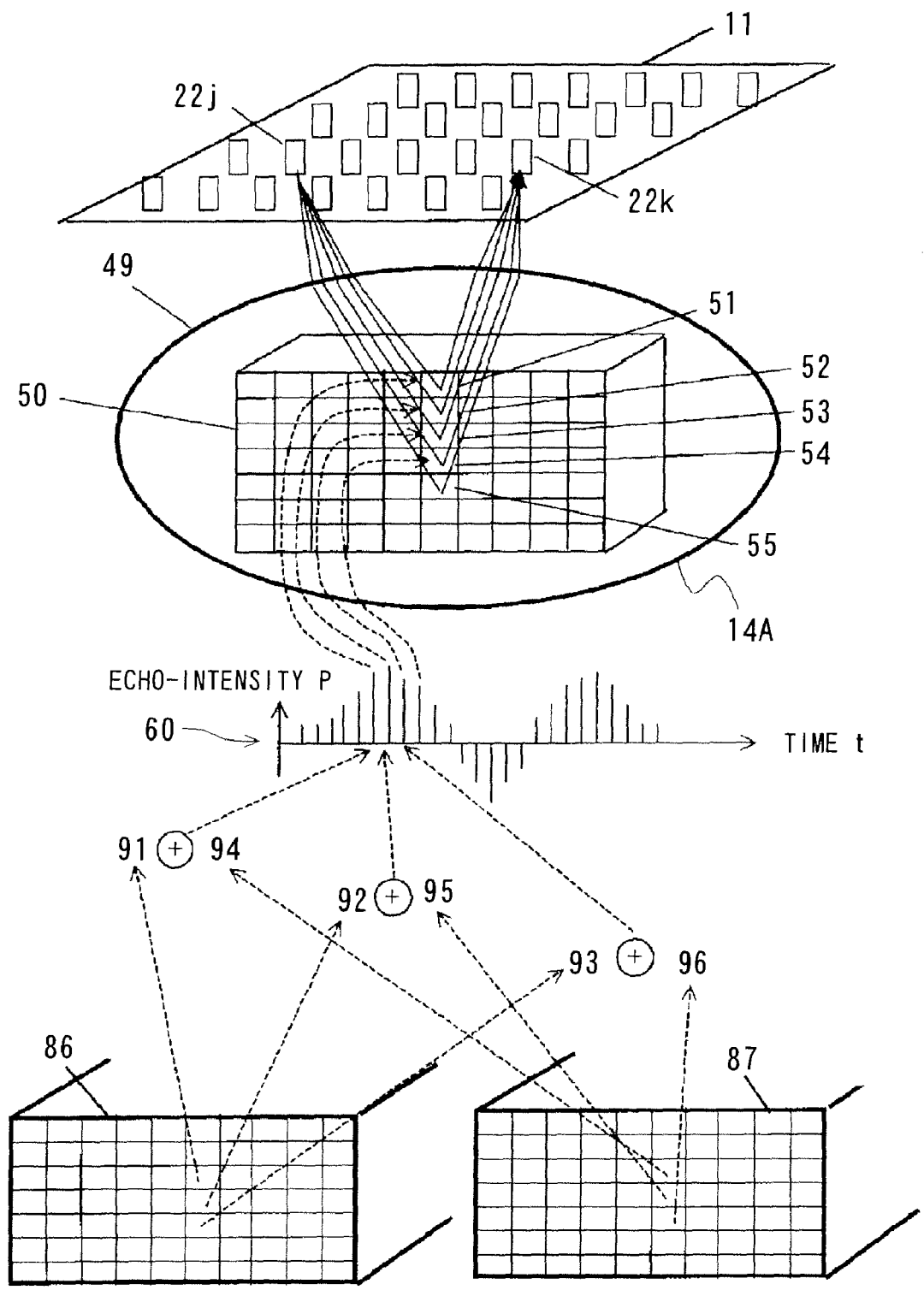
FIG. 7 is an explanation view showing an example of signal processing of a three-dimensional ultrasonic imaging apparatus according to a third embodiment of the present invention.

FIG. 7 is a modified example with regard to image synthesizing processing performed in an image synthesizing processing portion according to a third embodiment of the present invention. FIG. 7 shows an image synthesizing processing process by means of the ultrasonic wave U emitted and received by piezoelectric vibrators (j) 22*j* and (k) 22*k*.

After being refracted by the curved surface boundary 49, the ultrasonic waves U reach into the imaging region 50. Therefore, in table data (1) 86, there is stored one-way ultrasonic wave propagation time until the ultrasonic waves U reach to respective mesh elements of the imaging region 50, after being emitted from piezoelectric vibrator (1) 22-1 and being refracted by the curved surface boundary 49. Similarly, in table data (k) 87, there is also stored one-way ultrasonic wave propagation time until the ultrasonic waves U reach to respective mesh elements of the imaging region 50, after being emitted from piezoelectric vibrator (k) 22-*k* and being refracted by the curved surface boundary 49.

FIG. 7, as an example of image synthesizing processing, shows allocation processing of emission and reception waveforms 60 between piezoelectric vibrators (j) and (k) to the imaging mesh element (i) 51 to imaging mesh element (i+2) 52 - - - .

In the allocation processing to the imaging mesh element (i) 51, by adding propagation time (j, i) 91 stored in the (i)-th data of the table data U) 86 and propagation time (k, i) 94 stored in the (i)-th data of the table data (k) 87, two-way propagation time is obtained, or by selecting data having nearest delay time from the emission and reception waveforms 60 between piezoelectric vibrators (j) and (k), adding processing of the same to data in imaging mesh element (i) 51 in the imaging region 50 is performed.

In the allocation processing to the imaging mesh element (i+1) 52, by adding propagation time (j, i+1) 92 stored in the (i+1)-th data of the table data (j) 86 and propagation time (k, i+1) 94 stored in the (i+1)-th data of the table data (k) 95, two-way propagation time is obtained, or by selecting data having nearest delay time from the emission and reception waveforms 60 between piezoelectric vibrators (j) and (k), adding processing of the same to data in imaging mesh element (i+1) 52 in the imaging region 40 is performed.

Furthermore, by performing similar processing one after another with respect to the imaging mesh elements (i+2) 53 and (i+3) 54 so as to perform the processing with respect to all the imaging mesh elements in the imaging region 50, the image synthesizing processing by means of allocation of the emission and reception waveforms 60 between piezoelectric vibrators (j) and (k) is completed.

Thereafter, by changing the emission and reception waveforms to be allocated in the imaging region 50 and repeating similar processing with respect to all combinations of emission and reception, it is possible to complete the imaging of the internal state of the object to be inspected 14A.

Further, since in table the data (1) 84 to the table data (n) 88, data of one-way ultrasonic wave propagation times until the ultrasonic waves reach to respective mesh elements in the imaging region 50 after being emitted by piezoelectric vibrators (1) 22-1 to (n) 22-*n* is stored, one-way ultrasonic wave propagation times arranged in the depth direction also change continuously. Consequently, by subjecting the one-way ultrasonic wave propagation times of the table data (1) 84 to the table data (n) 88 to differencing processing with respect to the mesh elements arranged in the depth direction and storing them, the data capacity can be significantly compressed.

Figure 8:
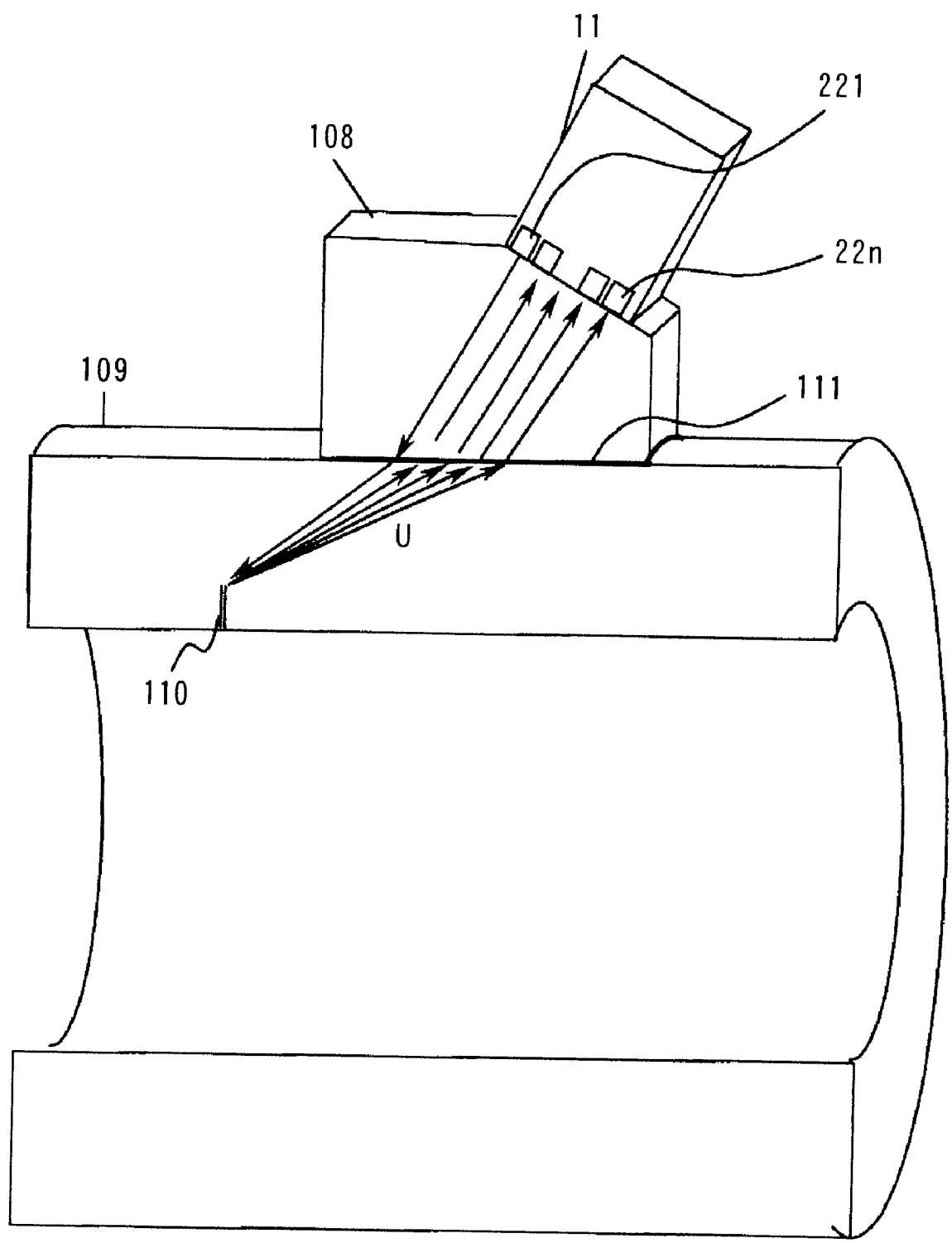
FIG. 8 is an explanation view showing an example of application to angle inspection of a three-dimensional ultrasonic imaging apparatus according to a fourth embodiment of the present invention.

FIG. 8 is a view of a configuration explaining an example to be applied to an angle inspection as a fourth embodiment of the present invention. As shown in FIG. 8, a resin-based shoe material 108 such as acrylic and polystyrene is brought into close contact with the tip of an ultrasonic transducer 11 via a liquid-state couplant 111 and further brought into close contact with an object to be inspected with a shape of a plane cylinder, or like shape by coating a couplant on the surface of the shoe material 108.

Herein, by tilting the angle of an attachment plane between the shoe material and the matrix transducer, ultrasonic waves emitted by piezoelectric vibrators (1) 22-1 to (n) 22*n* are caused to refract in the object to be inspected 109 to enter there in an oblique direction (for example, at an angle of 45° or 70°), and by receiving the ultrasonic waves U reflected by defects 110, the imaging of the defects 110 can be performed. In the condition of oblique incidence, three-dimensional image synthesizing according to an oblique angle can be performed by performing generation of table data (1) 84 to (n) 88 by an interface setting portion 83.

Figure 9:
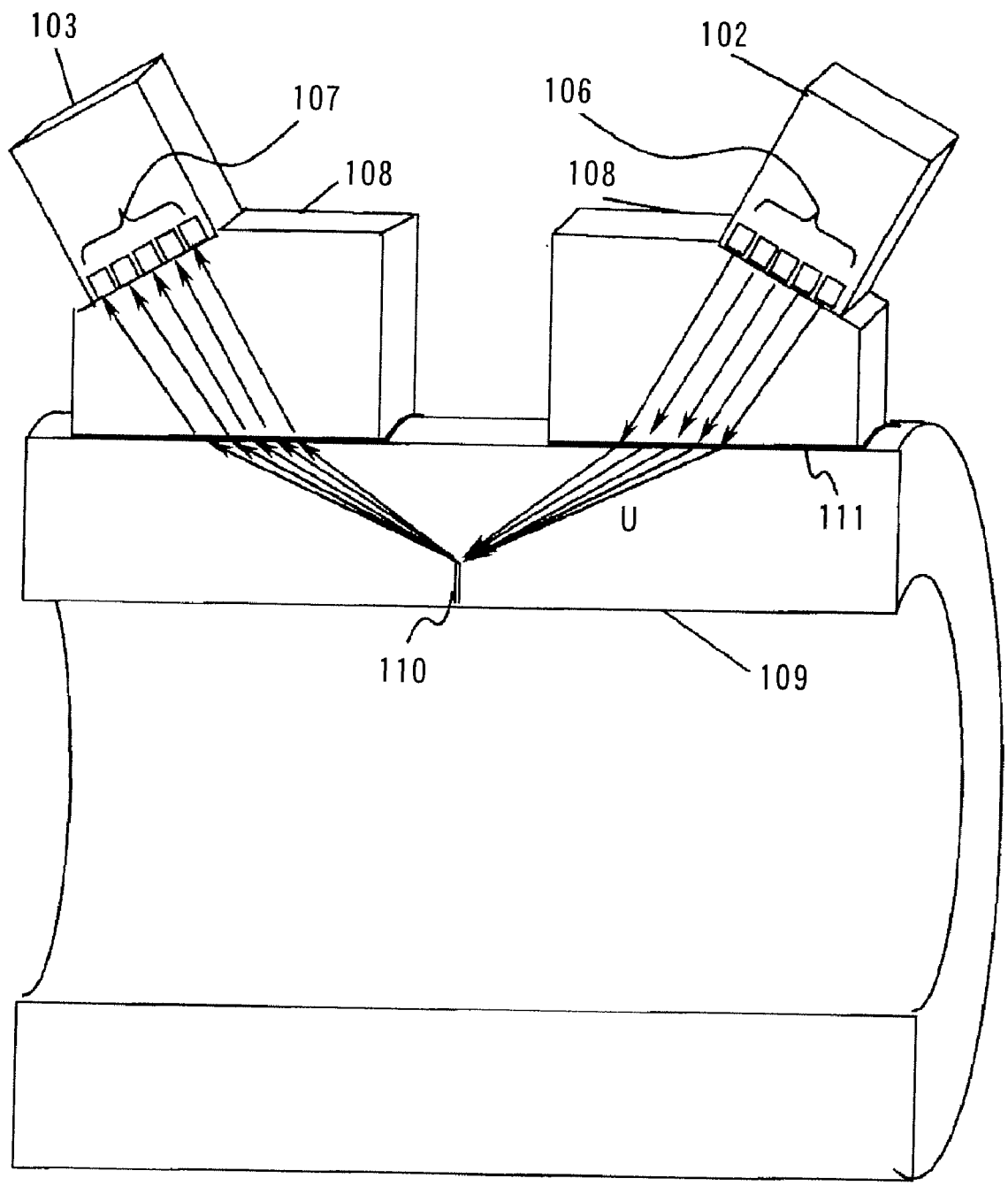
FIG. 9 is an explanation view showing imaging processing by a pair of matrix transducers divided into emission and reception in a three-dimensional ultrasonic imaging apparatus according to a fifth embodiment of the present invention.

FIG. 9 is a view of a configuration explaining an application example of the imaging by a pairs of three-dimensional transducers which are separated for emission and reception, as a fifth embodiment of the present invention. As shown in FIG. 9, a transducer 102 for emission and a transducer 103 for reception are arranged facing each other so that ultrasonic waves can be emitted and received by each transducer.

As for the transducer 102 for emission and the transducer 103 for reception, similar to the application example of the angle inspection, their tips are brought into close contact with shoe materials 108 having a same shape via liquid-state couplants 111, respectively. They are further brought into close contact with the object to be inspected 109 such as a pipe by coating a couplant on the surface of the shoe materials 108 and fixed to the object 109 asymmetrically so that defects 110 are sandwiched.

Herein, by tilting the angle of attachment planes between the shoe material 108 and the matrix transducer for emission 102 and the matrix transducer for reception 103, ultrasonic waves emitted by piezoelectric vibrators for emission 106 are caused to refract in the object to be inspected 109 to enter there in an oblique direction, and by receiving the ultrasonic waves U reflected by defects 110 by piezoelectric vibrators for reception 107, the imaging of the defects 110 can be performed. In the condition of oblique incidence, the imaging of the defects 110 can be performed.

In the condition of oblique incidence, by performing generation of the table data (1) 84 to (n) 88 by the matrix transducer for emission 102 and the matrix transducer for reception 103, three-dimensional image synthesizing by the matrix transducer for emission 102 and the matrix transducer for reception 103 can be performed.

Figure 10:
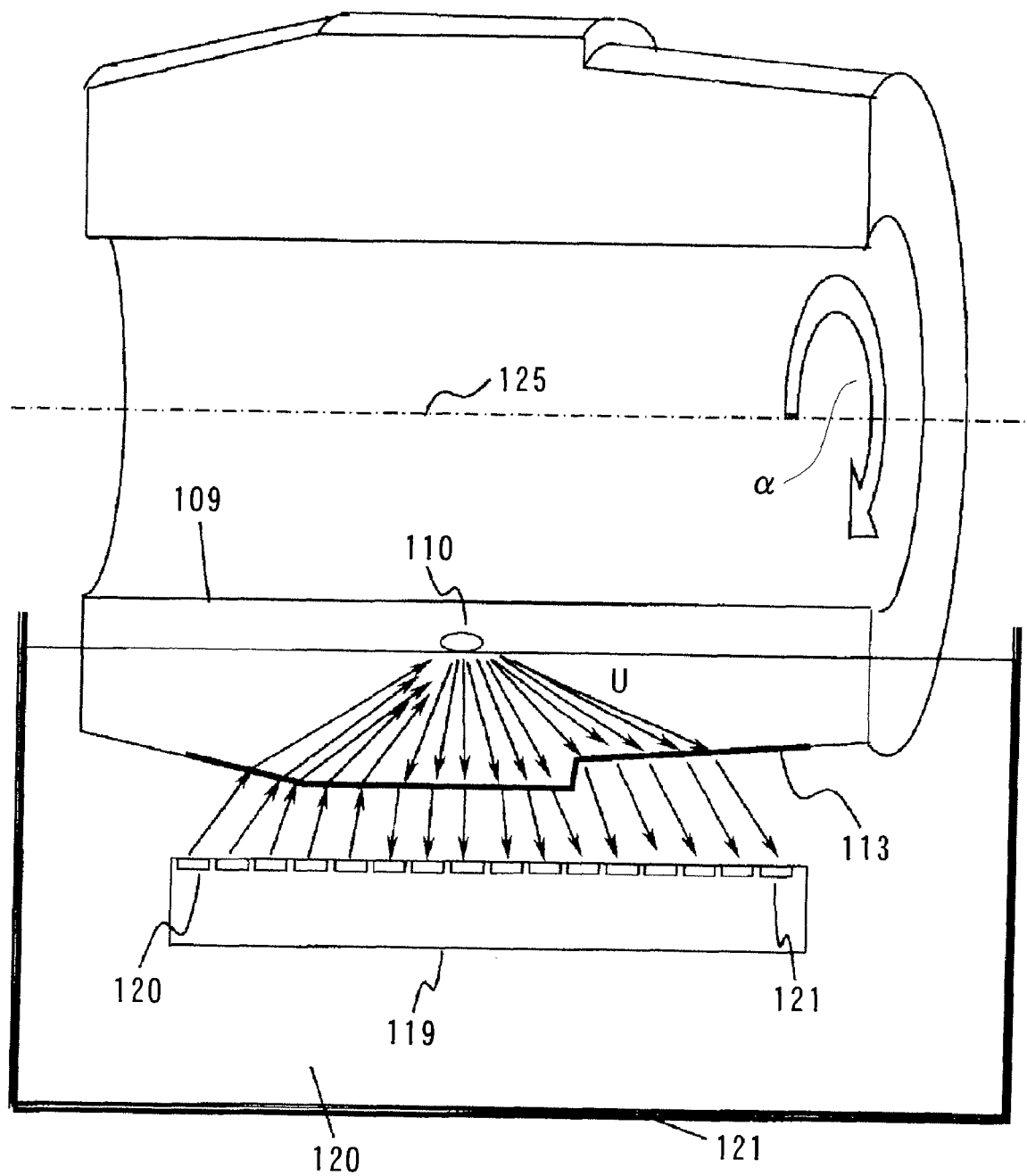
FIG. 10 is an explanation view showing an example of application of a linear array transducer in a three-dimensional ultrasonic imaging apparatus according to a sixth embodiment of the present invention.

FIG. 10 is a view of a configuration explaining an application example of inspection of an object having a cylinder shape by a linear array transducer 119, as a sixth embodiment of the present invention. As shown in FIG. 10, by emitting and receiving ultrasonic waves using the linear array transducer 119 in which n pieces of piezoelectric vibrators (1) 120 to (n) 121 are arranged in a straight line, two-dimensional cross-sections in the object to be inspected 109 can be imaged.

At that time, by setting a curved boundary 113 of the object to be inspected 109 at an interface setting portion and generating the table data (1) 84 to table data (n) 88, the internal inspection of an object to be inspected 109, whose cross-section has a constant shape, can be performed.

At that time, by performing the imaging of a cross-section by rotating the object to be inspected 109 around a central axis 125 as a center, every time when the rotation angle α changes by a constant value, and superposing a plurality of the obtained cross-sectional images and displaying the result, the three-dimensional imaging of the defects in the object to be inspected 109 can be performed.

Furthermore, by performing the imaging of the surface of the object to be inspected 109, every time when the rotation angle α changes by a constant value, and by processing the results and regenerating a curved boundary 113 in each case by a boundary extracting portion 82, and thus generating the table data (1) 84 to (n) 88, the internal inspection of the object to be inspected 109, whose cross-sectional shape changes, can also be performed.

The invention claimed is:

1. A three-dimensional ultrasonic imaging apparatus comprising:
    an ultrasonic transducer in which a plurality of piezoelectric vibrators are disposed in a matrix;
    a driving element selecting portion connected to the piezoelectric vibrators for selecting a piezoelectric vibrator to emit ultrasonic waves from the ultrasonic transducer by selectively driving a plurality of piezoelectric vibrators;
    a signal detecting circuit configured to cause an ultrasonic wave emitted by the piezoelectric vibrator selected by a starting element selecting portion to enter an object to be inspected via an acoustic wave propagating medium, to receive the reflected echo from the object to be inspected, and then to detect an electric signal corresponding to the reflected echo;
    a signal processing portion configured to receive the electric signal corresponding to the detected echo, to subject the electric signal to image synthesizing processing, and to generate three-dimensional imaging data; and
    a display device configured to receive the three-dimensional imaging data from the signal processing portion and to display the result of the image synthesizing processing,
    wherein the signal processing portion performs image synthesizing of a state of the object to be inspected on the basis of a detection time with which the signal detecting circuit detects the driving signal of the piezoelectric vibrators as a reflected echo and matrix special arrangement of the piezoelectric vibrators,
    wherein, in the signal processing portion, image synthesizing of surface shape and internal state of the object to be inspected is performed, for all of the piezoelectric vibrators constituting the ultrasonic transducer, by selecting imaging data from the electric signals of the reflected echo received from the object to be inspected via an acoustic propagating medium, on the basis of two-way ultrasonic wave propagation time data obtained by selecting a pair of pieces of table data corresponding to combination of emission and reception from a plurality pieces of table data in which ultrasonic propagation time of one propagating direction is stored and adding a pair of pieces of the table data to each of three-dimensional imaging mesh elements corresponding to the three-dimensional imaging data in the object to be inspected from the piezoelectric vibrators via the acoustic propagating medium,
    wherein the signal processing portion is composed of: a boundary setting portion for setting and memorizing the surface shape of the object to be inspected; a table data generating portion for storing the ultrasonic wave propagating times from the piezoelectric vibrator to the three-dimensional imaging mesh elements on the surface of the object to be inspected and inside the object via the acoustic propagating medium and generating table data in which the one-way ultrasonic wave propagating times are stored for all of the piezoelectric vibrators; and an image synthesizing portion for receiving waveform data recorded by a waveform storing memory and the table data via an A/D converter and synthesizing a three-dimensional image, and
    wherein the table data generating portion of the signal processing portion compresses data of the one-way ultrasonic wave propagation time table by storing the differencing processing result of the depth direction using a fact that the one-way ultrasonic wave propagation time changes continuously in the depth direction.

2. A three-dimensional ultrasonic imaging apparatus comprising:
    an ultrasonic transducer in which a plurality of piezoelectric vibrators are disposed in a matrix;
    a driving element selecting portion connected to the piezoelectric vibrators for selecting a piezoelectric vibrator to emit ultrasonic waves from the ultrasonic transducer by selectively driving a plurality of piezoelectric vibrators;
    a signal detecting circuit configured to cause an ultrasonic wave emitted by the piezoelectric vibrator selected by a starting element selecting portion to enter an object to be inspected via an acoustic wave propagating medium, to receive the reflected echo from the object to be inspected, and then to detect an electric signal corresponding to the reflected echo;
    a signal processing portion configured to receive the electric signal corresponding to the detected echo, to subject the electric signal to image synthesizing processing, and to generate three-dimensional imaging data; and
    a display device configured to receive the three-dimensional imaging data from the signal processing portion and to display the result of the image synthesizing processing,
    wherein the signal processing portion performs image synthesizing of a state of the object to be inspected on the basis of a detection time with which the signal detecting circuit detects the driving signal of the piezoelectric vibrators as a reflected echo and matrix special arrangement of the piezoelectric vibrators, wherein, in the signal processing portion, image synthesizing of surface shape and internal state of the object to be inspected is performed, for all of the piezoelectric vibrators constituting the ultrasonic transducer, by selecting imaging data from the electric signals of the reflected echo received from the object to be inspected via an acoustic propagating medium, on the basis of two-way ultrasonic wave propagation time data obtained by selecting a pair of pieces of table data corresponding to combination of emission and reception from a plurality pieces of table data in which ultrasonic propagation time of one propagating direction is stored and adding a pair of pieces of the table data to each of three-dimensional imaging mesh elements corresponding to the three-dimensional imaging data in the object to be inspected from the piezoelectric vibrators via the acoustic propagating medium, and wherein table data is generated by intimately fixing a wedge type shoe material to the ultrasonic transducer via a couplant so as to fix the ultrasonic transducer to the object to be inspected at an inclination angle, and the internal state of the object to be inspected is three-dimensionally visualized by emitting and receiving ultrasonic waves at the inclination angle.

3. A three-dimensional ultrasonic imaging apparatus comprising:

an ultrasonic transducer in which a plurality of piezoelectric vibrators are disposed in a matrix;

a driving element selecting portion connected to the piezoelectric vibrators for selecting a piezoelectric vibrator to emit ultrasonic waves from the ultrasonic transducer by selectively driving a plurality of piezoelectric vibrators;

a signal detecting circuit configured to cause an ultrasonic wave emitted by the piezoelectric vibrator selected by a starting element selecting portion to enter an object to be inspected via an acoustic wave propagating medium, to receive the reflected echo from the object to be inspected, and then to detect an electric signal corresponding to the reflected echo;

a signal processing portion configured to receive the electric signal corresponding to the detected echo, to subject the electric signal to image synthesizing processing, and to generate three-dimensional imaging data; and a display device configured to receive the three-dimensional imaging data from the signal processing portion and to display the result of the image synthesizing processing, wherein the signal processing portion performs image synthesizing of a state of the object to be inspected on the basis of a detection time with which the signal detecting circuit detects the driving signal of the piezoelectric vibrators as a reflected echo and matrix special arrangement of the piezoelectric vibrators, wherein, in the signal processing portion, image synthesizing of surface shape and internal state of the object to be inspected is performed, for all of the piezoelectric vibrators constituting the ultrasonic transducer, by selecting imaging data from the electric signals of the reflected echo received from the object to be inspected via an acoustic propagating medium, on the basis of two-way ultrasonic wave propagation time data obtained by selecting a pair of pieces of table data corresponding to combination of emission and reception from a plurality pieces of table data in which ultrasonic propagation time of one propagating direction is stored and adding a pair of pieces of the table data to each of three-dimensional imaging mesh elements corresponding to the three-dimensional imaging data in the object to be inspected from the piezoelectric vibrators via the acoustic propagating medium, and wherein table data is generated by providing a pair of the ultrasonic transducers, fixing the transducers to the surface of the object to be inspected so as to face each other symmetrically at an inclination angle, and using one of a pair of the ultrasonic transducers for emission and the other one for reception, and the internal state of the object to be inspected is three-dimensionally visualized.

4. A three-dimensional ultrasonic imaging apparatus comprising:

an ultrasonic transducer in which a plurality of piezoelectric vibrators are disposed in a matrix;

a driving element selecting portion connected to the piezoelectric vibrators for selecting a piezoelectric vibrator to emit ultrasonic waves from the ultrasonic transducer by selectively driving a plurality of piezoelectric vibrators;

a signal detecting circuit configured to cause an ultrasonic wave emitted by the piezoelectric vibrator selected by a starting element selecting portion to enter an object to be inspected via an acoustic wave propagating medium, to receive the reflected echo from the object to be inspected, and then to detect an electric signal corresponding to the reflected echo;

a signal processing portion configured to receive the electric signal corresponding to the detected echo, to subject the electric signal to image synthesizing processing, and to generate three-dimensional imaging data; and a display device configured to receive the three-dimensional imaging data from the signal processing portion and to display the result of the image synthesizing processing, wherein the signal processing portion performs image synthesizing of a state of the object to be inspected on the basis of a detection time with which the signal detecting circuit detects the driving signal of the piezoelectric vibrators as a reflected echo and matrix special arrangement of the piezoelectric vibrators, wherein, in the signal processing portion, image synthesizing of surface shape and internal state of the object to be inspected is performed, for all of the piezoelectric vibrators constituting the ultrasonic transducer, by selecting imaging data from the electric signals of the reflected echo received from the object to be inspected via an acoustic propagating medium, on the basis of two-way ultrasonic wave propagation time data obtained by selecting a pair of pieces of table data corresponding to combination of emission and reception from a plurality pieces of table data in which ultrasonic propagation time of one propagating direction is stored and adding a pair of pieces of the table data to each of three-dimensional imaging mesh elements corresponding to the three-dimensional imaging data in the object to be inspected from the piezoelectric vibrators via the acoustic propagating medium, wherein the signal processing portion visualizes the internal state of the object to be inspected by receiving the result of imaging the surface of the object to be inspected, generating a surface shape in a boundary extracting portion for automatically extracting the surface shape, and inputting the surface shape generated in the boundary extracting portion and coordination information of the piezoelectric vibrators into the table data generating portion, and wherein internal cross-sectional images of the object to be inspected are three-dimensionally imaged by using an ultrasonic transducer in which piezoelectric vibrators are arranged in a line so to be displayed by visualizing the internal cross-sectional images of the object to be inspected one by one and by superposing a plurality of the obtained cross-sectional images along the axis of the rotational angle, while two-dimensionally visualizing the surface shape of the object, receiving the obtained cross-sectional imaging data in a boundary extracting portion of the signal processing portion, automatically extracting the surface shape in the boundary extracting portion every time the object to be inspected is rotated by a constant angle and regenerating the (two-dimensional) table data.

5. A three-dimensional ultrasonic imaging apparatus comprising:

an ultrasonic transducer in which a plurality of piezoelectric vibrators are disposed in a matrix;

a driving element selecting portion connected to the piezoelectric vibrators for selecting a piezoelectric vibrator to emit ultrasonic waves from the ultrasonic transducer by selectively driving a plurality of piezoelectric vibrators;

a signal detecting circuit configured to cause an ultrasonic wave emitted by the piezoelectric vibrator selected by a starting element selecting portion to enter an object to be inspected via an acoustic wave propagating medium, to receive the reflected echo from the object to be inspected, and then to detect an electric signal corresponding to the reflected echo;

a signal processing portion configured to receive the electric signal corresponding to the detected echo, to subject the electric signal to image synthesizing processing, and to generate three-dimensional imaging data; and a display device configured to receive the three-dimensional imaging data from the signal processing portion and to display the result of the image synthesizing processing, wherein the signal processing portion performs image synthesizing of a state of the object to be inspected on the basis of a detection time with which the signal detecting circuit detects the driving signal of the piezoelectric vibrators as a reflected echo and matrix special arrangement of the piezoelectric vibrators, wherein, in the signal processing portion, image synthesizing of surface shape and internal state of the object to be inspected is performed, for all of the piezoelectric vibrators constituting the ultrasonic transducer, by selecting imaging data from the electric signals of the reflected echo received from the object to he inspected via an acoustic propagating medium, on the basis of two-way ultrasonic wave propagation time data obtained by selecting a pair of pieces of table data corresponding to combination of emission and reception from a plurality pieces of table data in which ultrasonic propagation time of one propagating direction is stored and adding a pair of pieces of the table data to each of three-dimensional imaging mesh elements corresponding to the three-dimensional imaging data in the object to be inspected from the piezoelectric vibrators via the acoustic propagating medium, wherein the signal processing portion visualizes the internal state of the object to be inspected by receiving the result of imaging the surface of the object to be inspected, generating a surface shape in a boundary extracting portion for automatically extracting the surface shape, and inputting the surface shape generated in the boundary extracting portion and coordination information of the piezoelectric vibrators into the table data generating portion, and wherein the table data generation portion of the signal processing portion compresses data of the one-way ultrasonic wave propagation time table by storing the differencing processing result of the depth direction using a fact that the one-way ultrasonic wave propagation time changes continuously in the depth direction.

6. A three-dimensional ultrasonic imaging apparatus comprising:

an ultrasonic transducer in which a plurality of piezoelectric vibrators are disposed in a matrix;

a driving element selecting portion connected to the piezoelectric vibrators for selecting a piezoelectric vibrator to emit ultrasonic waves from the ultrasonic transducer by selectively driving a plurality of piezoelectric vibrators;

a signal detecting circuit configured to cause an ultrasonic wave emitted by the piezoelectric vibrator selected by a starting element selecting portion to enter an object to be inspected via an acoustic wave propagating medium, to receive the reflected echo from the object to be inspected, and then to detect an electric signal corresponding to the reflected echo;

a signal processing portion configured to receive the electric signal corresponding to the detected echo, to subject the electric signal to image synthesizing processing, and to generate three-dimensional imaging data; and a display device configured to receive the three-dimensional imaging data from the signal processing portion and to display the result of the image synthesizing processing, wherein the signal processing portion performs image synthesizing of a state of the object to be inspected on the basis of a detection time with which the signal detecting circuit detects the driving signal of the piezoelectric vibrators as a reflected echo and matrix special arrangement of the piezoelectric vibrators, wherein, in the signal processing portion, image synthesizing of surface shape and internal state of the object to be inspected is performed, for all of the piezoelectric vibrators constituting the ultrasonic transducer, by selecting imaging data from the electric signals of the reflected echo received from the object to he inspected via an acoustic propagating medium, on the basis of two-way ultrasonic wave propagation time data obtained by selecting a pair of pieces of table data corresponding to combination of emission and reception from a plurality pieces of table data in which ultrasonic propagation time of one propagating direction is stored and adding a pair of pieces of the table data to each of three-dimensional imaging mesh elements corresponding to the three-dimensional imaging data in the object to be inspected from the piezoelectric vibrators via the acoustic propagating medium, wherein the signal processing portion selects and adds two pieces of table data corresponding to a pair of piezoelectric vibrators for emission and reception selected when the waveform data is collected one by one with respect to all waveform data collected among a plurality of table data generated in the table data generating portion, and on the basis of the two-way ultrasonic wave propagation time obtained from the addition result, the three-dimensional images is synthesized by subjecting the three-dimensional imaging mesh elements to allocation processing of the corresponding waveform data and addition processing one by one, and wherein the table data generation portion of the signal processing portion compresses data of the one-way ultrasonic wave propagation time table by storing the differencing processing result of the depth direction using a fact that the one-way ultrasonic wave propagation time changes continuously in the depth direction.

* * * * *